United States Patent [19]

Yensen

[11] Patent Number: 4,767,887
[45] Date of Patent: Aug. 30, 1988

[54] YENSEN 1A
[75] Inventor: Nicholas P. Yensen, Tucson, Ariz.
[73] Assignee: Salt Weeds, Tucson, Ariz.
[21] Appl. No.: 912,223
[22] Filed: Sep. 29, 1986
[51] Int. Cl.$^4$ .............................................. A01H 1/02
[52] U.S. Cl. ....................................................... 800/1
[58] Field of Search ............................ Plt./89; 800/1

Primary Examiner—Robert E. Bagwill
Attorney, Agent, or Firm—Cahill, Sutton & Thomas

[57] ABSTRACT

A variety, Yensen 1a, of *Distichlis palmeri*, characterized by vigorous growth in salty soils, high grain yield and ideal form for harvest, and for human consumption.

3 Claims, No Drawings

YENSEN 1A

BACKGROUND OF THE INVENTION

The present invention relates to a new and distinct variety of a plant of the family Poaceae and more particularly to a plant of the species Distichlis palmeri (Vasey) Fassett ex I. M. Johnston, commonly known as salt grass and is a perennial herbaceous flowering plant.

SUMMARY OF THE INVENTION

The new variety has a number of characteristics and desirable features distinguishing it as an improved variety. These characteristics are principally the vigorous growth, high yield and ideal form suitable for harvest.

DRAWING

The invention is illustrated in my copending application Ser. No. 901,315.

DESCRIPTION OF THE PREFERRED EMBODIMENTS

The new variety was noted in test plantings wherein approximately 100,000 seeds, seedlings and cuttings have been test planted under agricultural conditions on a total of 2.5 acres following over ten (10) years of study of salt-tolerant plants. The purpose of these large plantings was specifically to discover new varieties with crop potential and to learn their agronomic requirements. The new variety resulted from a bed seedling.

Wild plants of Distichlis palmeri produce from near zero to four grams of grain per square meter. Yensen 1a can produce well over ten grams of grain per square meter. The optimum yields with respect to fertilizer and water levels of Yensen 1a are not known at this time.

The new variety was first noted for its vigorous growth and ideal form and later for its high yield of grain on relatively short stalks. The stalks are erect and the grain heads are of a suitable height for combine harvest.

The new variety is being reproduced via rhizomes in Tucson, Ariz., where a number of other varieties are also being observed.

The following is a detailed description of the new variety:

Parentage: A seedling from a harvested caryopses (seeds) of Distichlis palmeri. The harvested caryopses from which the Yensen 1a variety emerged were among literally millions of harvested caryopses which were then selected for size and weight. While approximately 100,000 caryopses have been so selected and test planted, the particular test planting from which Yensen 1a emerged had approximately 3,000 caryopses. This test planting was in plot number 2 ... of 9 test plots planted at Tucson, Ariz. These test plots were subjected to various stresses, e.g. water, temperature, salts, etc. such that only 0.1% to 1% of the caryopses reached maturity. The plants that survive this rigorous selection process are often phenotypically similar. This may be true in part due to similar genetic combinations that can survive the same rigorous selection process, and in part to the harvested caryopses being frequently derived from a few phenotypically similar parents. Due to (1) the nature of the selection process wherein massive numbers of caryopses are utilized, and (2) the heavy selection pressures, it is not practical to follow individual caryopses and their lineages.

Propagation: To date all rhizomes, shoots, and tillers have held true to the distinguishing characteristics of the initial plants and it is expected that at least 90% of the female plants from caryopses will be phenotypically similar to the distinguishing characteristics of the initial plants as they are described herein.

Culms: Rigid, erect, occasionally branched, glabrous, 20-50 cm high depending on rhizome age at inflorescence, 2-3 mm in diameter. The color of Yensen 1a is not significantly different from some other varieties.

Rhizomes: Thick and scaled at nodes.

Blades: Firm, rigid, ascending, pointed and pungent, involute (especially upon drying), distichous, glabrous to slightly puberulent, 3-5 mm basal width, 20-30 veins at base, typically 30-80 mm in length.

Sheath: Glabrous to slightly puberulent, with a tuft of wooly hairs at either side of the mouth, ligule smooth with pubescence apically.

Inflorescence:
- *Panicle.*—Erect, compoundly branched (often branched in two's), 4-8 cm in length and does not extend beyond the leaves;
- *Spikelet.*—With 5-9 flowers, subtending "bracts" infertile, 20-40 mm in length, 6-10 mm in width;
- *Florets.*—lemma 10-15 mm in length decreasing slightly apically on the spikelet, 4-6 feint veins on either side of a weak keel;

palea 9-11 mm in length, length decreasing slightly apically on the spikelet;

- *Caryopses.*—6-11 mm in length (including the bifurcated style), length decreasing slightly apically on the spikelet, 1-2 mm in width, 1-2 mm in height; embryo cover 2-4 mm in length; ventral surface indented with a longitudinal groove (except in unusually well-filled caryopses); anterior seed coat longitudinally wrinkled and posterior portion wrinkled into two rounded ventral keels and one rounded dorsal keel which extends to the bifurcation of the styles; surface texture with numerous longitudinal striae and light vertical rugae, glabrous, colored a coriaceous brown and may be darker anteriorly and lighter posteriorly.

I claim:

1. A new and distinct plant, Yensen 1a, a variety of Distichlis palmeri, which is principally characterized by vigorous growth, high grain yield and ideal form for harvesting.

2. Plant material of plant variety of claim 1 selected from the group consisting of caryopses, tillers and rhizomes.

3. A new and distinct plant, Yensen 1a, which is principally distinguished by blade glabrous to slightly puberulent with a 3-5 mm basal width and with 20-30 basal veins, typically 30-80 mm in length; blade sheath glabrous to slightly puberulent; ligule smooth with pubescence apically; panicle 4-8 cm in length with spikelets 20-40 mm in length and 6-10 mm in width; lemma 10-15 mm in length; decreasing slightly apically on the spikelet and with 4-6 feint veins on either side of the weak keel; palea 9-11 mm in length, length decreasing slightly apically on the spikelet.

* * * * *